(12) United States Patent
Uemura et al.

(10) Patent No.: US 11,389,055 B2
(45) Date of Patent: Jul. 19, 2022

(54) OPHTHALMOLOGICAL IMAGE OBSERVATION METHOD AND OPHTHALMOLOGICAL IMAGE OBSERVATION APPARATUS

(71) Applicant: NIDEK CO., LTD., Aichi (JP)

(72) Inventors: Haruka Uemura, Aichi (JP); Riccardo Ferraris de Gaspare, Albignasego (IT)

(73) Assignee: NIDEK CO., LTD., Aichi (JP)

( * ) Notice: Subject to any disclaimer, the term of this patent is extended or adjusted under 35 U.S.C. 154(b) by 13 days.

(21) Appl. No.: 17/010,003

(22) Filed: Sep. 2, 2020

(65) Prior Publication Data

US 2021/0068649 A1 Mar. 11, 2021

(30) Foreign Application Priority Data

Sep. 4, 2019 (JP) .............................. JP2019-161605

(51) Int. Cl.
| | | |
|---|---|---|
| G06T 3/00 | (2006.01) | |
| A61B 3/00 | (2006.01) | |
| G06F 3/048 | (2013.01) | |
| G06T 1/00 | (2006.01) | |
| G06T 7/38 | (2017.01) | |

(52) U.S. Cl.
CPC ............ *A61B 3/0058* (2013.01); *G06F 3/048* (2013.01); *G06T 1/0007* (2013.01); *G06T 3/0068* (2013.01); *G06T 7/38* (2017.01); *G06T 2200/24* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2009/0276725 A1* | 11/2009 | Glaser-Seidnitzer | ... G16Z 99/00 715/771 |
| 2018/0064409 A1* | 3/2018 | Schmidt-Richberg | ....................... G06K 9/3233 |
| 2019/0343381 A1* | 11/2019 | Dastmalchi | ............. G06T 15/08 |

FOREIGN PATENT DOCUMENTS

| | | |
|---|---|---|
| EP | 3 300 654 A2 | 4/2018 |
| JP | 2018-51245 A | 4/2018 |

* cited by examiner

*Primary Examiner* — Yi Wang
(74) *Attorney, Agent, or Firm* — Sughrue Mion, PLLC

(57) ABSTRACT

A computer displays a part or the entirety of a first image, which is one of the plurality of registered images, in a first display region on a monitor, receives a switching instruction to switch an image displayed in the first display region, in a state where the first image is displayed in the first display region, from the first image to a second image which is one of the plurality of registered images and is different from the first image, and displays a part or the entirety of the second image adjusted based on the displacement information to match a region on the subject eye indicated in the first display region with the first image, in the first display region based on the switching instruction.

13 Claims, 6 Drawing Sheets

OPHTHALMOLOGICAL IMAGE OBSERVATION METHOD AND OPHTHALMOLOGICAL IMAGE OBSERVATION APPARATUS

CROSS-REFERENCE TO RELATED APPLICATION

This application claims priority from Japanese Patent Application No. 2019-161605 filed on Sep. 4, 2019, the entire subject-matter of which is incorporated herein by reference.

TECHNICAL FIELD

The present disclosure relates to an ophthalmological image observation method and an ophthalmological image observation apparatus.

BACKGROUND

In an image diagnosis in the field of ophthalmology, there are cases in which a subject eye is diagnosed and observed in various directions by comparing a plurality of images captured at different times or in different imaging methods.

For example, in JP-A-2018-51245 discloses a method in which a plurality of images each of which are a plurality of fundus front images imaging the same fundus region and captured at different times or in different imaging methods are arranged and displayed on a monitor side by side.

In the method described above, the plurality of images displayed on the monitor are arranged at positions apart from each other. Therefore, it is difficult for the examiner to intuitively grasp a correspondence relationship of the regions between the images.

SUMMARY

An object of the present disclosure is to provide an ophthalmological image observation method and an ophthalmological image observation apparatus that are capable of displaying a plurality of two-dimensional ophthalmological images for enabling an examiner to compare those images in a favorable and easy manner.

An ophthalmological image observation method of according to the present disclosure causes an ophthalmological image observation apparatus to execute:

an acquisition step of acquiring a plurality of two-dimensional ophthalmological images obtained by imaging a subject eye;

a registration step of registering a plurality of registered images which are images for comparison display, from the plurality of two-dimensional ophthalmological images;

a displacement information acquisition step of acquiring displacement information that represents a displacement between the registered images; and a comparison display step of performing display processing of the registered image, in which the comparison display step includes:

a first display control step of displaying a part or an entirety of a first image which is one of the plurality of registered images, in a first display region on a monitor;

a switching instruction receiving step of receiving a switching instruction to switch an image displayed in the first display region, in a state where the first image is displayed in the first display region, from the first image to a second image which is one of the plurality of registered images and is different from the first image; and a second display control step of displaying a part or an entirety of the second image adjusted based on the displacement information to match a region on the subject eye indicated in the first display region with the first image, in the first display region based on the switching instruction.

An ophthalmological image observation apparatus according to the present disclosure executes the ophthalmological image observation method described above.

DETAILED DESCRIPTION

Hereinafter, one embodiment in the present disclosure will be described. First, an ophthalmological image observation system according to the embodiment will be described with reference to FIG. 1. The ophthalmological image observation system is used for imaging a subject eye and display a two-dimensional ophthalmological image as a result of imaging.

Figure 1:
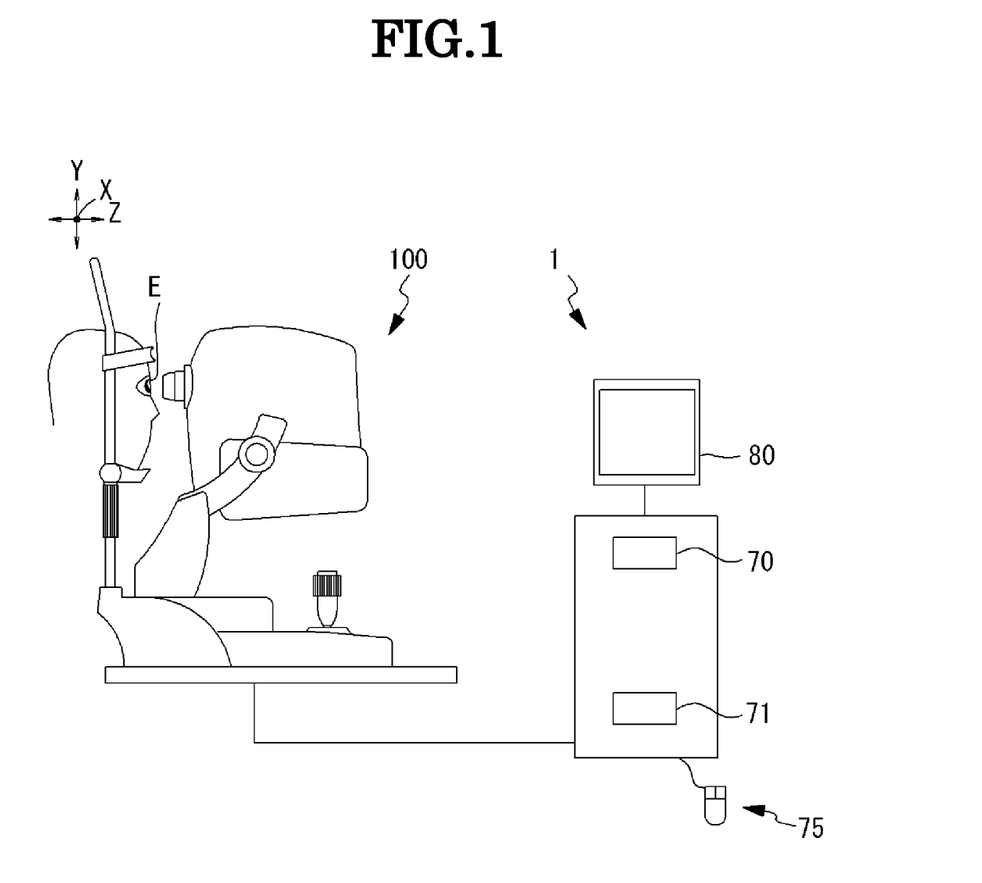
FIG. 1 is a block diagram illustrating an outline of an ophthalmological image observation system according to an embodiment.

In the present embodiment, the ophthalmological image observation system includes a computer (an ophthalmological image observation apparatus) 1 and an ophthalmologic imaging apparatus 100. The computer 1 and the ophthalmologic imaging apparatus 100 are connected by wire or wirelessly and can communicate with each other. In this way, the two-dimensional ophthalmological image can be transmitted and received from the ophthalmologic imaging apparatus 100 to the computer 1. An ophthalmological image observation program according to the embodiment is stored in a non-volatile memory that can be read by a processor of the computer 1. In the present embodiment described below, the ophthalmologic imaging apparatus 100 and the computer 1 are separate bodies. However, the two devices may be integrated.

As above, in the description of the embodiment, as an example, a case where the computer 1 and the ophthalmologic imaging apparatus 100 have a one-to-one relationship will be described. However, it is not necessarily limited thereto. For example, the computer 1 may be Capable of communicating with a plurality of ophthalmologic imaging apparatuses, and the computer 1 may be able to acquire the two-dimensional ophthalmological images captured by each of a plurality of ophthalmologic imaging apparatuses, <Ophthalmologic Imaging Apparatus>

The ophthalmologic imaging apparatus 100 includes at least an imaging optical system (not illustrated). In this imaging optical system, after a fundus of a subject eye is irradiated with light, return light from the fundus is received by a light receiving element. In the present embodiment, a two-dimensional ophthalmological image is formed based on a light reception signal from the light receiving element. The two-dimensional ophthalmological image is formed b an image processing circuit (for example, an IC, a processor, or the like) of the ophthalmologic imaging apparatus 100. The image processing circuit does not need to be provided in the ophthalmologic imaging apparatus 100. For example, the image processing circuit of the computer 1 may also serve as the image processing circuit of the ophthalmologic imaging apparatus 100.

In the present embodiment the ophthalmologic imaging apparatus 100 captures a two-dimensional ophthalmological image. The two-dimensional ophthalmological image may be, for example, a front image or a tomographic image (cross-sectional image) of one cut surface. In the description below, the description will be made under an assumption that the fundus front image is used (acquired and processed) as an example of the two-dimensional ophthalmological image unless otherwise specified.

The ophthalmologic imaging apparatus 100 may be a fundus camera, a scanning fundus imaging apparatus (for example, a scanning light ophthalmoscope: SLO), an optical coherence tomography (OCT), or a combination of any of those described above.

The ophthalmologic imaging apparatus 100 may capture the fundus front image with using a plurality of imaging methods. At least one of the wavelength band of the light used, the substance used for imaging (in a case of contrast imaging), and the imaging principle may be different between each of the imaging methods.

For example, the ophthalmologic imaging apparatus 100 may be able to capture at least one of an infrared light reflection image (hereinafter, referred to as an IR image) and a multiple color visible light reflection image (hereinafter, referred to as a color image). Furthermore, a monochromatic visible light reflection image may be captured. In this case, the reflection image may be captured with each of equal to or more than two colors of visible light.

In addition, for example, the ophthalmologic imaging apparatus 100 may be capable to capture a fluorescence contrast image by an imaging method of either indocyanine green contrast imaging (ICGA) or fluorescein contrast imaging (FA). Two types of fluorescence contrast images may be captured at the same time by injecting two types of contrast agents at the same time. Hereinafter, an image based on the fluorescence emission of the indocyanine green is referred to as an ICGA image, and an image based on the fluorescence emission of fluorescein is referred to as an FA image.

In addition, for example, the ophthalmologic imaging apparatus 100 may be able to capture a spontaneous fluorescence image (FAF image). As the FAF image, a B-FAF image using blue light as excitation light and a G-FAF image using green light as excitation light may be captured.

Furthermore, for example, the ophthalmologic imaging apparatus 100 may be able to capture an OCT front image. The OCT front image may be, for example, an en-face image obtained by averaging three-dimensional OCT data in the depth direction, or a front image of a specific layer. In addition, these OCT front images may be functional OCT images, or may be motion contrast images (MC images), which is a more specific example. The motion contrast image is generated based on the motion contrast OCT data. As the motion contrast image, for example, a pseudo angiographic image (OCT angio image) can be obtained.

A part or an entirety of the color image, fluorescence contrast image (FA image and ICGA image), FAF image, and OCT front image may be captured at the same time with the IR image. The "same time" here is not limited to a completely same time. That is, a slight time difference is allowed. The time difference may be set, for example, within a range in which significant eye movement does not occur while two types of fundus front images are captured.

<Computer>

The computer 1 acquires at least various fundus front images captured by the ophthalmologic imaging apparatus 100, and displays the images on the monitor 80. The computer 1 includes at least an arithmetic control unit 70. The arithmetic control unit 70 is a processor of the computer 1. The arithmetic control unit 70 may be configured with a CPU, RAM, ROM, and the like, as illustrated in FIG. 1. The arithmetic control unit 70 performs a display control of the fundus front image and various processing relating to the fundus front image based on the ophthalmological image observation program.

As illustrated in FIG. 1, the arithmetic control unit 70 of the computer 1 is connected to a memory 71, an operation unit 75, the monitor 80, the ophthalmologic imaging apparatus 100 and the like via a data bus and the like.

In the present embodiment, the memory 71 is a nonvolatile storage device. For example, a hard disk, a flash memory, or the like can be applied as the memory 71. In the present embodiment, the ophthalmological image observation program is stored in the memory 71 in advance. The memory 71 may be rewritable. In this case, various fundus front images acquired from the ophthalmologic imaging apparatus 100 may be stored in the memory 71 as described in the application examples below. However, the fundus front image may be stored in a memory (not illustrated) separate from the memory in which the ophthalmological image observation program is stored.

The operation unit 75 is an input interface of the computer 1. The arithmetic control unit 70 receives a signal according to an operation input to the operation unit 75.

For convenience, various operations in the description below are based on an assumption that a mouse is used as the operation unit 75. However, the operation unit 75 may be various other devices. For example, at least one of a touch pad and a keyboard may be used as the operation unit 75.

The monitor 80 is used as a display unit (display device) of an image captured by the ophthalmologic imaging apparatus 100 in the present embodiment. The monitor 80 may be, for example, a general-purpose monitor or a monitor installed in the apparatus. Instead of the monitor 80, another display device such as a head mounted display may be used as the display unit.

<Description of Operation>

Next, an operation of the ophthalmological image observation system will be described with reference to the flowchart illustrated in FIG. 2. Bach processing in the flowchart may be executed by the computer 1 based on the ophthalmological image observation program.

<S1: Acquisition Step>

First, a plurality of fundus front images are captured by the ophthalmologic imaging apparatus 100. The captured fundus front image is stored in the memory of the apparatus in association with the imaging method and the identification information indicating the image capturing date and time. In addition, regarding the fluorescence contrast image and the IR image acquired at the same time as the fluorescence contrast image, information indicating a measurement time of the contrast timer at the time of imaging may be further associated.

Thereafter, the captured fundus front image is acquired by the computer 1 (S1). The "acquisition" here is that the target data (here, the data of the fundus front image) is stored in the memory (here, the memory 71) accessible from the processor of the computer 1. The imaging methods may be different between a part or an entirety of the plurality of fundus front images. In addition, a part or an entirety of the plurality of fundus front images may have different image capturing dates or different time phases in contrast. In addition, the computer 1 may acquire various information associated with the image (for example, the imaging method, the imaging date and time, and the measurement time of the contrast timer) together with the fundus front image.

<S2: Registration of Registered Image>

Next, from a plurality of fundus front images acquired as a result of the processing in S1, a plurality of registered images (also referred to as comparison images) are registered, which are images for comparison display (S2). At this time, it is preferable that the imaging area on the subject eye is substantially the same between the registered images. Of course, the imaging areas may be substantially the same among the plurality of fundus front images acquired as a result of S1.

The registered image may be selected, for example, from a plurality of fundus front images acquired as a result of S1, based on a registration operation by the examiner. In this case, the computer 1 may display an operation screen for receiving the registration operation on the monitor 80, and may receive the registration operation via the operation screen. At this time, a plurality of fundus front images acquired as a result of S1 may be displayed on the operation screen. In addition, on the operation screen, it may be possible to individually receive an operation regarding whether or not to register each fundus front image as a registered image.

Figure 3:
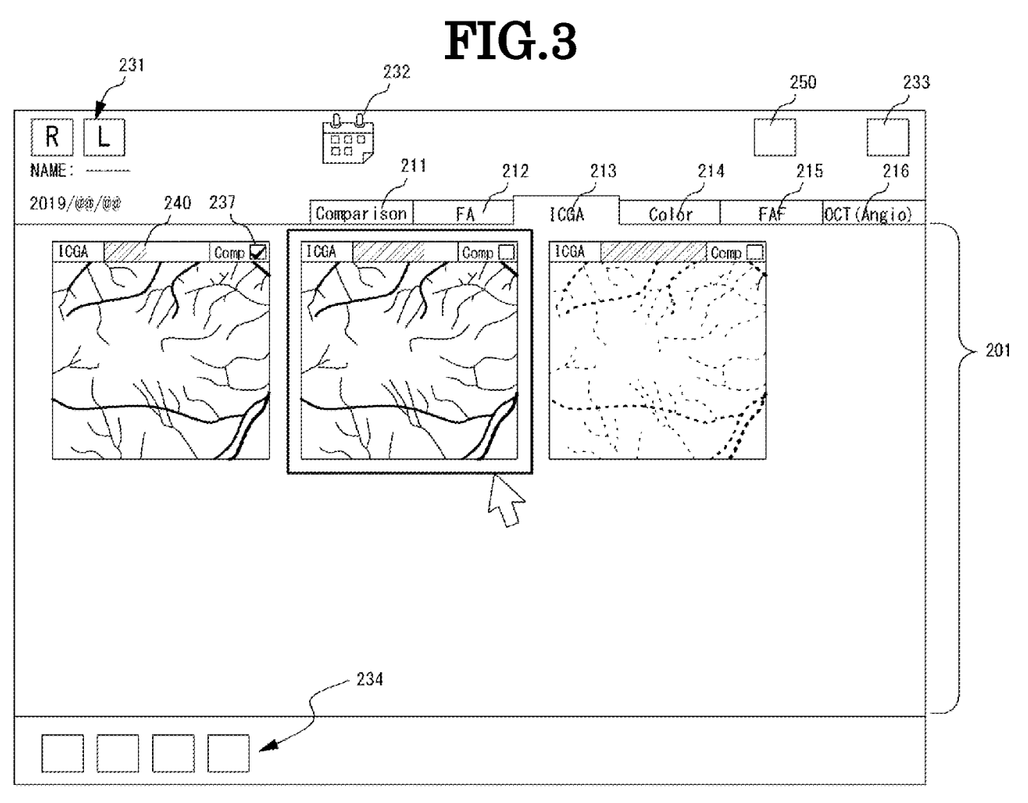
FIG. 3 is a diagram illustrating a first display-mode on a first viewer screen.
Figure 4:
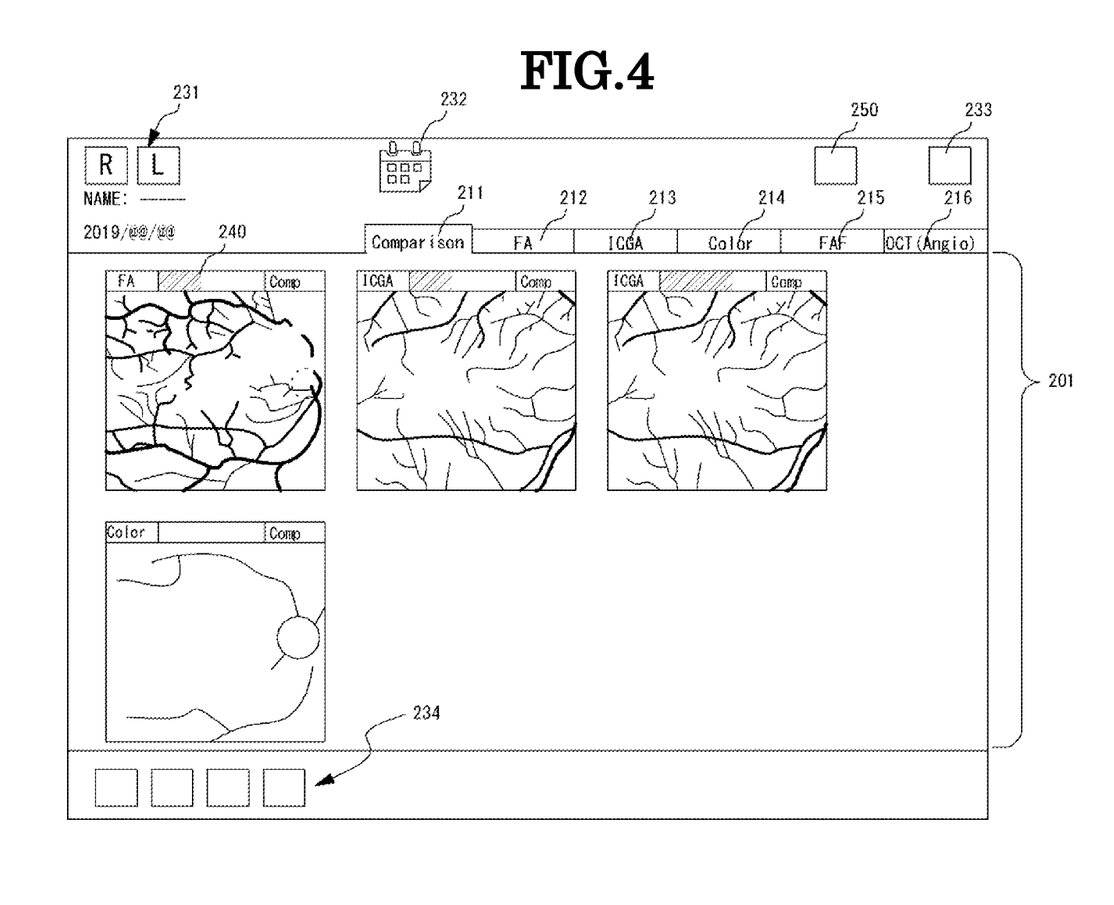
FIG. 4 is a diagram illustrating a second display mode in the first viewer screen.

FIG. 3 and FIG. 4 illustrate the examples of the operation screens. The operation screens illustrated in FIG. 3 and FIG. 4 is also referred to as a first viewer screen. On the operation screens illustrated in FIG. 3 and FIG. 4, various widgets are arranged in addition to a plurality of fundus front images. The widget here is a generic term for GUI interface parts (UI parts), and is also referred to as a control. As specific examples of the widget, various ones such as buttons, sliders, check boxes, text boxes, and like are known.

On the operation screens in FIG. 3 and FIG. 4, a plurality of tabs 211 to 216 are arranged above the display region 201. A content of the display region 201 (refer to FIG. 3 and FIG. 4, respectively) are switched according to a tab selection operation.

The tabs 212 to 216 (an ICGA tab 212, an FA tab 213, a color tab 214, an FAF tab 215, and an OCT (Angio) tab 216) correspond to the respective imaging methods. By selecting any one of the tabs 212 to 216, the fundus front image by any of the imaging methods (here, the imaging method selected via tab) among the plurality of fundus from images captured by different imaging methods, is selectively displayed side by side on the display region 201 (see FIG. 3)

At this time, the operation for registering the fundus front image as a registered image can be received for each fundus front image displayed in the display region 201. As illustrated in FIG. 3, a checkbox 237 may be arranged around each fundus front image in the display region 201 (upper part in the drawing). The checkbox 237 is selected and the checked fundus front image is registered as a registered image.

When the tab 211 is selected, the computer 1 displays the registered images registered in advance on the display region 201 side by side (refer to FIG. 4). At this time, a plurality of fundus from images captured by different imaging methods may be arranged in a mixed manner. Since each fundus front image is picked up in advance for each imaging method, it is easy to view even if a plurality of fundus front images captured by different imaging methods are arranged on the display region 201 in a mixed manner.

However, as illustrated in FIG. 4, in a display mode in which a plurality of fundus front images are displayed on one screen side by side, it is difficult for the examiner to intuitively grasp the correspondence relationship between regions while comparing the images. That is, in such a display mode, since the respective images are arranged at the positions apart from each other, in another image, it is difficult to accurately specify a region corresponding to one region of a certain image. In addition, when the difference between the corresponding regions is minute, it is difficult to grasp the difference.

Figure 5:
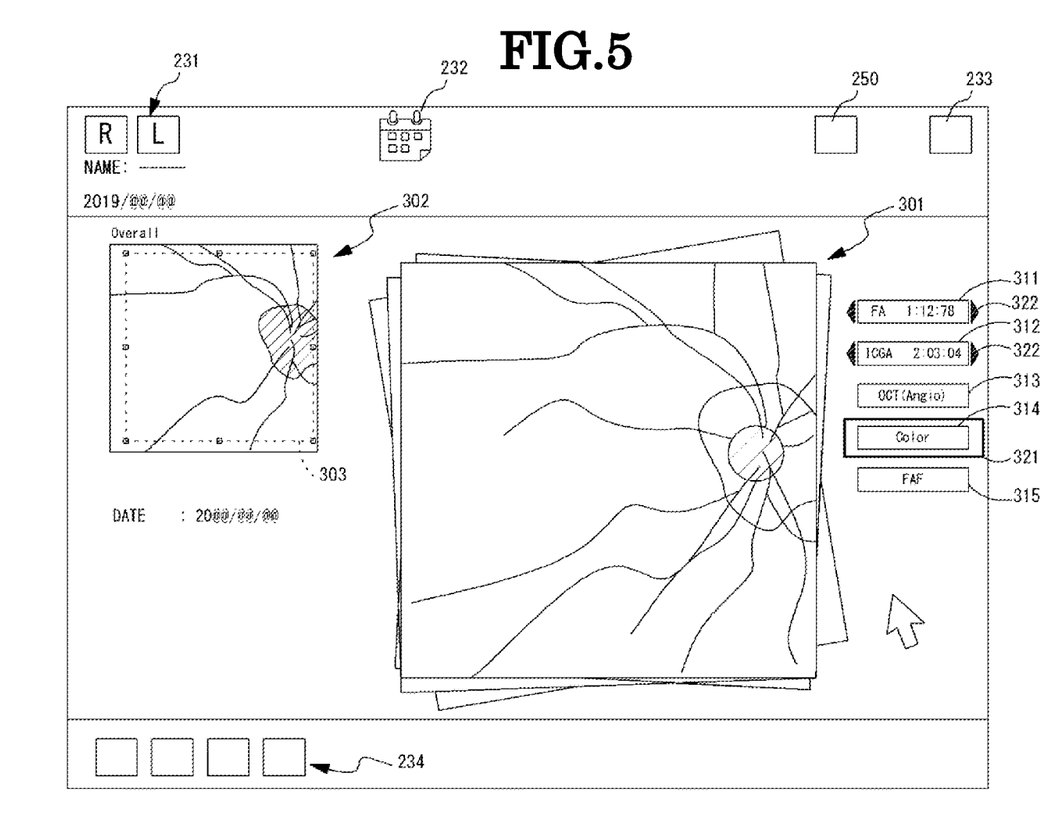
FIG. 5 is a diagram illustrating the first display mode in a second viewer screen.
Figure 6:
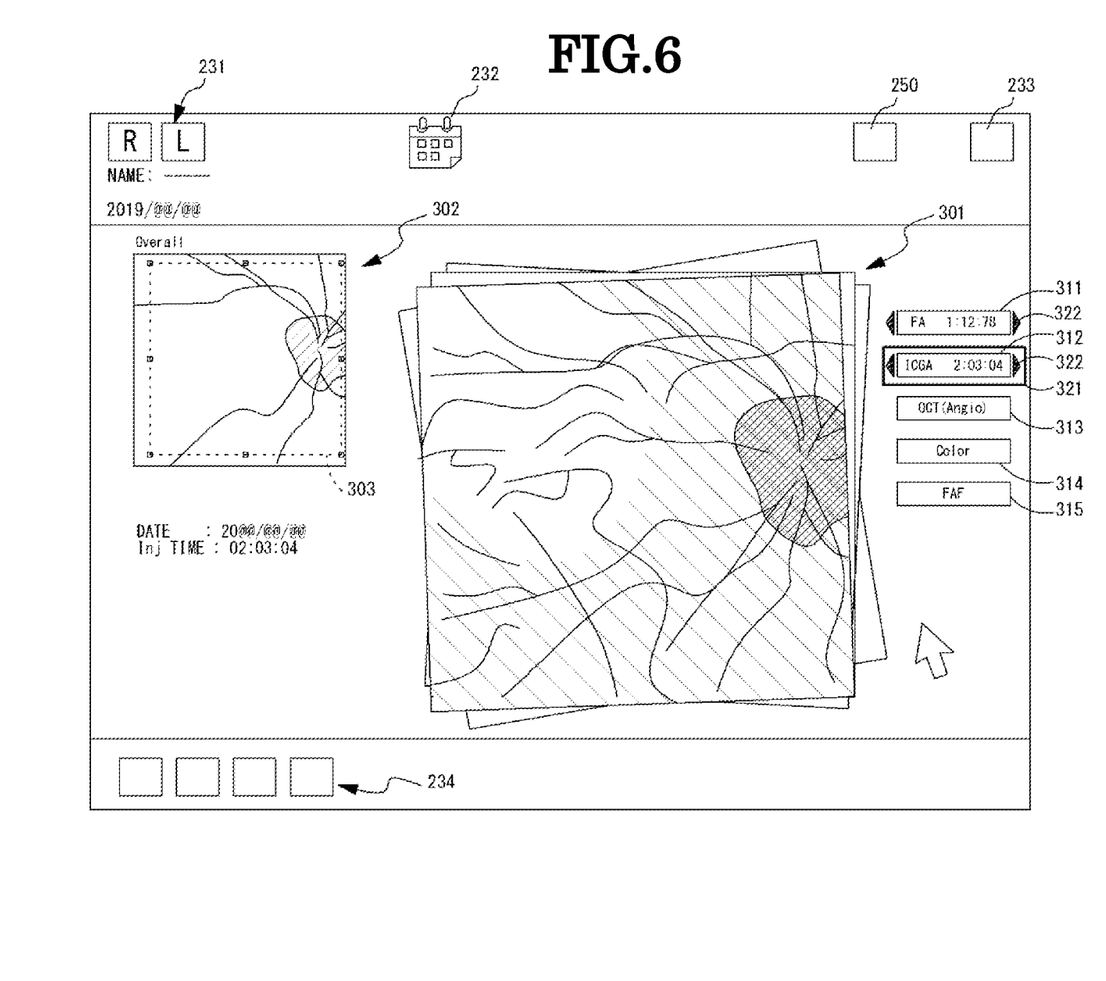
FIG. 6 is a diagram illustrating the second display mode in the second viewer screen.

On the other hand, in the present embodiment, a comparison display is performed for the registered images as illustrated in FIG. 5 and FIG. 6. For example, the comparison display may be performed by selecting the button 250 on the operation screen.

<S3: Detection Processing for Displacement Information Between Registered Images>

When the comparison display is performed, the displacement information between the registered images is acquired by the computer 1. The displacement information includes at least the displacement (an amount of positional deviation) between the registered images. The displacement information may additionally include information relating to a rotation, distortion, and magnification.

At this time, the displacement between the IR images captured at the time same as that of each registered image may be applied as the displacement between the registered images (specifically, for example, refer to JP-A-2016-59400 by the present applicant). The displacement between the IR images may be acquired based on various matching processing such as the normalized cross-correlation method and the phase-only correlation method. In addition, not between the IR images captured at the same time, but the displacement information may be acquired by performing the matching processing between the registered image itself (or a specific wavelength component in the registered image) and another registered image (or that specific wavelength component thereof) or an IR image captured at the time as that of another registered image.

Figure 2:
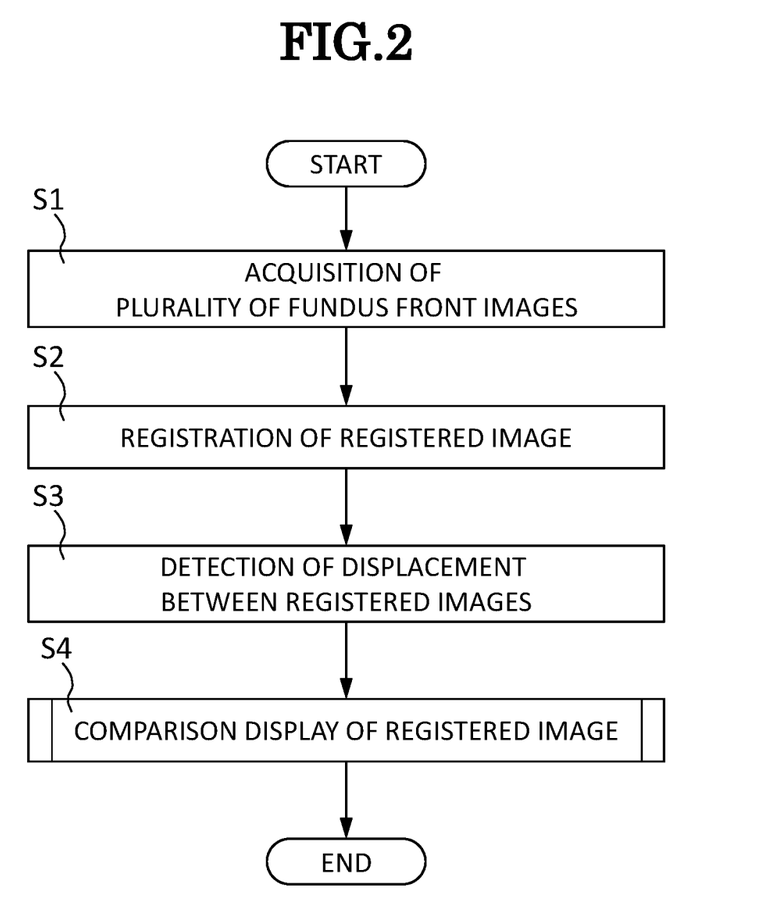
FIG. 2 is a flowchart illustrating a flow of processing based on an ophthalmological image observation method.

The flowchart illustrated in FIG. 2 indicates that such detection processing for displacement information is performed after registration of the registered image. However, it is not necessarily limited thereto. For example, the displacement information may be acquired in advance before the operation screen of FIG. 3 or FIG. 4 is displayed. In this case, the displacement information between the fundus front images acquired by the processing in S1 may be acquired in advance as a result of the matching processing as described above. In addition, in this case, the above-described matching processing does not need to be necessarily performed by the computer 1, and may be performed by the ophthalmologic imaging apparatus 100, and then, the displacement information obtained as a result thereof may be acquired by the computer 1 in a state of being associated with each image.

In addition, a following method may be applied as a method for obtaining the displacement information between the registered images. That is, after performing a multiple point selection (plotting) from the corresponding points in the two registered images based on the selection operation, the displacement (for example, positional deviation, rotation, distortion, and magnification) between the two registered images may be calculated and acquired by the computer 1 based on the displacement between the corresponding points. As the corresponding points, for example, characteristic points common to the two registered images such as a macula, an optic disk, and the intersection of blood vessels may be selected.

<S4: Comparison Display of Registered Image>

The comparison display of the registered image registered in advance is performed in a mode as illustrated in FIG. 5 or FIG. 6. The screen at this time is referred to as a comparison screen (also referred to as a second viewer screen) for convenience. At least a comparison display region 301 is set on the screen.

<First Display Control Step>

First, any one of a plurality of registered images registered in advance (referred to as a first image for convenience) is alternatively displayed in the comparison display region 301. At this time, the entire image of the first image or a part of the image may be displayed in the comparison display region 301.

A reference display region 302 may be further set on the second viewer screen. The reference display region 302 is arranged at a position different from that of the comparison display region 301. A reference image may be displayed in the reference display region 302. The reference image is referenced by the examiner in order to grasp the position on the fundus corresponding to the registered image displayed in the comparison display region 301.

For example, the entire image of any registered image may be displayed as the reference image. The reference image may be a fundus image according to a predetermined imaging method. For example, the entire color fundus image may be displayed as a reference image, or an IR image captured at the same time as any of the registered images may be displayed.

The reference image may be constant (may be fixed) regardless of the display content in the comparison display region 301. At this time, one or both of the imaging method and the display area in the reference image may be constant. For example, the entire image of the color fundus image may be displayed as the reference image regardless of which imaging method the registered image displayed in the comparison display region 301 is captured.

In the reference image, the region on the subject eye indicated in the comparison display region 301 may be emphasized. For example, in FIG. 6, the display area of a comparison image in the comparison display region 301 is indicated and emphasized by a selection frame 303 as the position information indicated in the reference display region 302. The examiner can grasp which position on the fundus is drawn in the comparison display region 301 by the reference image and the selection frame 303.

In the description of the present embodiment, unless otherwise specified, the reference image is described as being a fundus image captured at the same angle of view as any of the registered images, but not necessarily limited thereto. The reference image may be a fundus image captured at a different angle of view (preferably wider angle) than the registered image. By using the wider-angle fundus image as the reference image, the examiner can more easily grasp a location on the fundus indicated by the registered image via the reference image.

In the description of the present embodiment, unless otherwise specified, the reference image is any image captured by the ophthalmologic imaging apparatus 100. However, the present embodiment is not limited thereto, and it may be at fundus image of the subject eye captured by an imaging apparatus separate from the ophthalmologic imaging apparatus 100.

<Area-change Instruction Receiving Step>

Here, the computer 1 may receive an area-change instruction for changing the display area of the first image in the comparison display region 303 (area-change instruction receiving step). As an example, the reference image may image may be used to change the display area of the first image.

For example, the area-change instruction may be received based on the operation to the selection frame 303 (an example of the widget) described above. The selection frame 303 may be deformed (here, enlarged or reduced) by an operation via a pointing device (specifically, a drag operation with respect to a control point, or the like). The display area of the comparison image in the comparison display region 301 may be changed in conjunction with the operation to the selection frame 303. The operation via the selection frame 303 is only an example of a method of receiving an area-change instruction, and the area-change instruction may be received based on another operation. When the area-change instruction is received, the display area of the first image in comparison display region 301 is changed based on the area-change instruction, and as a result, the desired region of the examiner is displayed in comparison display region 301.

When enlarging (zooming in) a part of the registered image in the comparison display region 303, the predetermined location of the registered image may be enlarged and displayed. At this time, a specific location such as the macula portion and the optic disk portion may be predetermined as a target of the enlarged display (zoom display). The specific location may be automatically detected by image processing or may be manually set by the examiner. In addition, a plurality of locations may be predetermined as the targets for enlarged display (zoom display), and the locations to be enlarged may be switched based on the second area-change instruction.

<Switching Instruction Receiving Step>

The computer 1 can receive a switching instruction used for switching the image displayed in the display region 301 to another registered image (referred to as the second image for convenience) from the first image while the first image is displayed in the display region 301. In the present embodiment, the switching instruction may be received based on various operations. Hereinafter, an operation input to the operation unit 75 for the switching instruction will be referred to as a switching operation.

For example, on the second viewer screen, image selection buttons 311 to 315 are provided as widgets for receiving the switching instructions. The image selection buttons 311 to 315 illustrated in FIG. 5 and FIG. 6 are provided for each imaging method in the registered image, for example. However, not necessarily limited thereto, the image selection button may be provided for each registered image.

The image selection buttons 311 to 315 (FA button 311, ICGA button 312, OCT (Angio) button 313, color button 314, and FAF button 315) illustrated in FIG. 5 and FIG. 6 correspond to respective imaging methods, respectively. By selecting any one of the image selection buttons 311 to 315, the registered image by one of the imaging methods (here, the imaging method selected via the tab) among a plurality of registered images captured by different imaging methods is selectively displayed in the comparison display region 301. On the selected button among the image selection buttons 311 to 315, a selected mark 321 is displayed. When a first switching operation is received, the selected mark 321 is moved between the image selection buttons 311 to 315 according to an order of the image selection buttons 311 to 315. The mark 321 may be looped between the bottom button and the top button. As the selected mark 321 moves, the registered image displayed in the comparison display region 301 is switched.

In addition, when there are a plurality of registered images for one imaging method, a mark 322 is added. When a second switching operation is received in a state in which the button with mark 322 selected, the plurality of registered images by the selected imaging method are switched and displayed in a capturing order (that is, in chronological order) in the comparison display region 301. At this time, the second switching operation may be an operation different from the first switching operation.

Specific examples of each switching operation (the operation input to the operation unit 75 for the switching instruction) will be described later.

<Second Display Control Step>

In a second display control step, the newly selected registered image (referred to as a second image for convenience) is switched from the first image and displayed in the comparison display region 301 based on the switching instruction described above (for example, FIG. 5→FIG. 6). At this time, a part or the entirety of the second image, which is adjusted to match the region on the subject eye indicated in the comparison display region 301 with the first image, is displayed in the comparison display region 301. The adjustment is performed based on the displacement information acquired in the processing in S3 (for example, the displacement information of each of the first image and the second image).

When the display area of the first image in the comparison display region 101 is changed based on the area-change instruction (for example, the instruction by the operation of the selection frame 303), in the second display control step, the display area of the second image is adjusted by taking over the changed display area of the first image, and then, the second image is displayed in the comparison display region 301. That is, a part or the entirety of the second image, which the region on the subject eye indicated in the comparison display region 301 is adjusted so as to match the first image immediately before switching.

As an example, in the second viewer screen in FIG. 5 and FIG. 6, the positional relationship between each of the registered images is adjusted in advance (before the switching instruction is input) based on the displacement information. In detail, position alignment processing based on displacement information is performed for each registered image, and each registered image is arranged in different layers in a state of being aligned state. In such a display mode, the selected registered image is arranged and displayed on the forefront layer, and thus, the selective display of the registered image can be realized. At this time, the transparency of the selected registered image may be adjusted so that the image arranged on the rear side layer becomes impermeable. However, not limited thereto, and the position alignment processing may be performed between the first image and the second image each time a switching instruction is received.

In the position alignment processing, the position alignment between the first image and the second image may be performed only in the area corresponding to the comparison display region 301. In this case, the position alignment is performed only in a part of the image, not in the entire image. If a visual fixation is deviated between the first image and the second image, distortions that are different in each image occur. The difference in the distortions between the first image and the second image reduces the accuracy of position alignment between the entire images. Therefore, by performing the position alignment between the first image and the second image by limiting the area corresponding to the comparison display region 301, it is possible to prevent a decrease in the accuracy of the position alignment due to the above distortions. The deviation of the visual fixation has a greater influence on the difference in distortion in the fundus peripheral region than in the fundus central region. Accordingly, the larger the angle of view of the registered image (the first image and second image), the more useful it is to perform the position alignment by limiting the area corresponding to comparison display region 301.

The second image displayed in the comparison display region 301 can also be used as a new first image. In other words, by receiving various switching operations described in <Switching Instruction Receiving Step>, another registered image can be displayed as a new second image (or as a next first image) in the comparison display region 301).

As described above, in the present embodiment, when the image displayed in the comparison display region 301 is switched from the first image to the second image, the second image is adjusted to match the region on the subject eye indicated in the comparison display region 301 with the first image immediately before switching. Therefore, the correspondence relationship of each region between the first image and the second image can be easily and intuitively grasped by the examiner to grasp. In addition, the difference between the first image and the second image can be easily grasped by the examiner as a change in visual information. As a result, the examiner can favorably compare a plurality of registered images by switching the display in the present embodiment.

<Regarding Preferable Switching Operation>

It is desirable that the examiner switches between the first image and the second image while gazing at the comparison display region 301 and displays images. On the other hand, each switching operation in the present embodiment may be an operation that does not require a movement of the pointer outside the region of the comparison display region 301 on the monitor 80 each time the registered image displayed in the comparison display region 301 is switched. For example, each switching operation may be an operation that can be input regardless of the position of the pointer. A specific example of such a switching operation may be a mouse wheel scrolling operation. In this case, the registered images displayed in the comparison display region 301 in response to the wheel scroll may be switched and displayed in a predetermined switching order. In addition, for example, each switching operation may be an operation that can be input while the pointer is arranged at a fixed position. In this case, each time the fixedly arranged button is clicked on the monitor 80, the registered images displayed in the comparison display region 301 may be switched and displayed in a predetermined switching order. Alternatively, if it is needed to move the pointer in every switching operation, the switching operation may be limited to the operation within the comparison display region 301. For example, when the operation unit 75 is a touch panel, a swipe operation in the comparison display region 301 may be used as the switching operation.

By the fact that the switching operation is an operation that does not require the movement of the pointer outside the region of comparison display region 301, the examiner can compare a plurality of registered images while gazing at the comparison display region 301. As a result, it is possible for the examiner to favorably grasp the difference between the plurality of registered images.

In addition, it is preferable that each switching operation is a one-action operation. The one-action operation here is the only operation required for switching the registered images on the comparison display region 301. In other words, in switching the registered image, confirmation is not required after the operation is performed. Since the confirmation is not required for each switching operation, it is possible for the examiner to easily compare the plurality of registered images by the switching and display in the comparison display region 301 without cutting the line of sight from the comparison display region 301.

<Setting of Switching Order>

In the present embodiment, if the switching order between the two registered images are separated from each other by two or more, in comparing the two registered images, while the two registered images are displayed in the comparison display region 301, it becomes necessary to display another image or to perform the selection operation of the image selection buttons 311 to 315 by moving the pointer. Therefore, it is considered that it is difficult to grasp the correspondence relationship and the difference compared with the case where the switching order between the two registered images is continuous.

On the other hand, in the present embodiment, a priority (switching order) of displaying in the display region 301 among the registered images registered by the processing of S2 may be replaced based on a replacement instruction. By making the switching order of registered images that the examiner wants to compare be continuous, the two registered images can be directly switched and displayed. As a result, the switching display in the comparison display region 301 makes it easier for the examiner to favorably compare registered images.

For example, in the second viewer screen illustrated in FIG. 5 and FIG. 6, an arrangement order of the image selection buttons 311 to 315 may be replaced by a drag and drop. The switching order between the registered images captured by different imaging methods may be set (changed) according to the arrangement order of the image selection buttons 311 to 315. Of course, this is just an example, and the replacement instruction of the switching order may be received by other methods. For example, the initial setting of the switching order between the registered images captured by different imaging methods may be set in advance. This is considered to be useful when the type of the registered images is fixed in the facility.

In addition, the switching order between each of the registered images may be automatically adjusted in consideration of the imaging methods for each of the registered images. For example, the imaging methods of the fluorescence contrast image (FA image and ICGA image) and the OCT angio image are the same in a point that a blood flow is contrasted, and thus, it is expected to be possible to more multilaterally grasp the state of the blood flow. Therefore, when the fluorescence contrast image (FA image and ICGA image) and the OCT angio image are mixed in the registered image, the switching order may be adjusted so as to be adjacent switching orders.

In addition, in the reflection image, the switching order may be adjusted according to an invasion depth at the fundus caused by the wavelength of the illumination light. For example, when a reflection image for each of a plurality of monochromatic lights having different wavelength ranges is registered as a registered image, the switching order may be adjusted in the order of the reflection image having a shallower invasion depth of the illumination light to the reflection image having a deeper invasion depth, or vice versa. As a specific example, a case where three types of reflection images by the light of each wavelength of R (red), G (green), and B (blue) are registered as the registered images will be described. Here, the R (red) light reaches the deep layer of the retina. The B (Hue) light reaches the surface layer of the retina. The R (red) light reaches the deep layer of the retina. The G (green) light reaches an intermediate depth between the B (blue) light and the R (red) light. Therefore, the switching order may be set in the order of the reflection image by R (red)→reflection image by G (green) →reflection image by B (blue), or vice versa.

<Various Widgets in First and Second Viewer Screens>

As other widgets, a left and right eye switching button 231, a follow-up observation button 232, a data output button 234, an image edit button 235, and the like are arranged in each viewer screen illustrated in FIG. 3 to FIG. 6.

The left and right eye switching button 231 is operated to switch the fundus front image displayed on the viewer screen between an image of the right eye and an image of the left eye.

The follow-up observation button 232 is operated to display the fundus front images having different imaged dates on the display region 201 on the first viewer screen in parallel. After operating the follow-up observation button 232, an operation for specifying the imaged date can be further received. In the present embodiment, the fundus front image having the imaged date specified at this time is displayed in parallel with the fundus front image already displayed in the display region 201. In this way, each of the fundus front images captured on different imaged dates is registered as the registered images, and thus, it is possible to compare (perform the follow-up observation) via the second viewer screen.

The data output button 233 is operated to output the fundus front image selected, edited, and the like on the viewer screen. For example, when the button 233 is operated, the fundus front image may be output in a predetermined report format. The output may be a display output, a data output, or a print output.

The image edit button 234 is operated when editing the fundus front image displayed in the display region which is selected by the examiner. Through the image edit button 234, for example, execution of various image processing such as brightness, contrast correction, gamma correction, sharpening, and smoothing may be received.

Modification Example

As described above, the description has been made based on the embodiment, but, the present disclosure is not limited to the above embodiment. The present disclosure may include various modifications to the above-described embodiment <Comparison Display with Other Modality>

In addition to the embodiment described above, a map indicating a retinal visibility for each location (in other words, retinal visibility distribution in the retina) may be displayable in the comparison display region 301. The visibility distribution may be, for example, a test result of any one of a perimeter, an ERG (electroretinogram), and an FRG (functional retinography). The perimeter may be a static perimeter (for example, Humphrey perimeter, a microperimeter, or the like) or a dynamic perimeter (for example, a Goldman perimeter, or the like).

In this case, the visibility distribution may be superimposed on the registered image displayed in the comparison display region 301. At this time, any of the registered image or the visibility distribution may be transparently displayed.

The test results additionally displayed in the comparison display region are not limited to the visibility distribution, and may be test results by other modalities.

<Presetting of Conditions to Register in Registered Image>

In the embodiment described above, in order to register various fundus front images acquired by the computer 1 as the registered images, the registration operation on the viewer screen is required for each image.

On the contrary, by setting conditions for registering the registered image in advance, among the fundus front images acquired by the computer 1, the image that meet the conditions may be registered as the registered image. Such an image may be displayed as the registered image on the viewer screen without requiring a registration operation via the viewer screen.

The preset conditions may be selectable from, for example, the following three conditions. These conditions may be set for each imaging method.

First condition: all the images captured by a specific imaging method are registered as the registered images.

Second condition: a fluorescence contrast image obtained at a predetermined elapsed time is registered as the registered image.

Third condition: the pre-registration of the registered image is not performed.

The first condition is suitable for the color image, the spontaneous fluorescence image, and the IR image. Since the number of times above-described images are captured in one day is generally smaller than that of the fluorescence contrast image, by registering any of each fundus front image as the registered image in the default setting, the load to the examiner required for setting the registered image is reduced.

The second condition is useful when the contrast examination is routinely worked in the facility. The elapsed time in the second condition may be set to any time, or a plurality of times may be set.

What is claimed is:

1. An ophthalmological image observation method of causing an ophthalmological image observation apparatus to execute:
   an acquisition step of acquiring a plurality of two-dimensional ophthalmological images obtained by imaging a subject eye;
   a registration step of registering a plurality of registered images, which are images for comparison display, from the plurality of two-dimensional ophthalmological images;
   a displacement information acquisition step of acquiring displacement information that represents a displacement between registered images; and
   a comparison display step of performing display processing of the registered images,
   wherein the comparison display step includes:
   a first display control step of displaying a part or an entirety of a first image, which is one of the plurality of registered images, in a first display region on a monitor;
   a switching instruction receiving step of receiving a switching instruction to switch an image displayed in the first display region, in a state where the first image is displayed in the first display region, from the first image to a second image which is one of the plurality of registered images and is different from the first image; and
   a second display control step of displaying a part or an entirety of the second image adjusted based on the displacement information to match a region on the subject eye indicated in the first display region with the first image, in the first display region based on the switching instruction; and
   wherein the first image is captured from a first imaging method and the second image is captured from a second imaging method that is different from the first imaging method.

2. The ophthalmological image observation method according to claim 1,
   wherein the comparison display step further includes:
   an area-change instruction receiving step of receiving an area-change instruction to change a display area of the first image in the first display region,
   in the first display control step, in a case where the area change instruction is received, the display area of the first image in the first display region is changed based on the area-change instruction, and
   in the second display control step, a display area of the second image is adjusted by taking over the changed display area of the first image, and the second image is displayed in the first display region.

3. The ophthalmological image observation method according to claim 1,
   wherein in the comparison display step, position information of a region on the subject eye indicated in the first display region is further displayed in a second display region set at a display position different from the first display region on the monitor.

4. The ophthalmological image observation method according to claim 3,
   wherein in the comparison display step, a third image is displayed as the position information displayed in the second display region, the third image being a two-dimensional ophthalmological image and emphasizing the region on the subject eye indicated in the first display region.

5. The ophthalmological image observation method according to claim 1,
   wherein information indicating an imaging method of the registered image is associated with each of the registered images, and
   in the comparison display step, information indicating an imaging method of the registered image displayed in the first display region is displayed with the registered image.

6. The ophthalmological image observation method according to claim 5,
   wherein a switching order of displaying each registered image between the registered images in the first display region is adjusted in consideration of an imaging method of each of the registered images.

7. The ophthalmological image observation method according to claim 1, wherein in the acquisition step, two or more two-dimensional ophthalmological images having different imaged dates or different imaged time phases are acquired.

8. The ophthalmological image observation method according to claim 1,
wherein a switching operation, which is an operation input to an operation unit for the switching instruction, is an operation that does not require a movement of a pointer in a region outside the first display region on the monitor each time the registered image displayed in the first display region is switched.

9. The ophthalmological image observation method according to claim 1, further comprising:
a switching order replacement step of receiving a replacement instruction to replace a switching order of displaying each registered image between the registered images in the first display region, and replacing the switching order based on the replacement instruction.

10. The ophthalmological image observation method according to claim 1,
wherein a switching order of displaying each registered image between the registered images in the first display region is adjusted in consideration of an imaging method of each of the registered images.

11. An ophthalmological image observation apparatus that executes the ophthalmological image observation method according to claim 1.

12. The ophthalmological image observation method according to claim 1, wherein the two-dimensional ophthalmological images obtained by imaging a subject eye are fundus front images.

13. The ophthalmological image observation method according to claim 1, wherein in the comparison display step, the switching instruction is received via a widget provided for each imaging method of the registered image.

* * * * *